US007199110B2

(12) United States Patent
Borgens et al.

(10) Patent No.: US 7,199,110 B2
(45) Date of Patent: Apr. 3, 2007

(54) METHOD OF TREATMENT FOR SPINAL CORD INJURY

(75) Inventors: Richard B. Borgens, Delphi, IN (US); Scott A. Shapiro, Indianapolis, IN (US)

(73) Assignees: Purdue Research Foundation, West Lafayette, IN (US); Indiana University Research & Technology Corp., Indianapolis, IN (US)

( * ) Notice: Subject to any disclaimer, the term of this patent is extended or adjusted under 35 U.S.C. 154(b) by 223 days.

(21) Appl. No.: 10/748,572

(22) Filed: Dec. 30, 2003

(65) Prior Publication Data

US 2004/0214790 A1    Oct. 28, 2004

Related U.S. Application Data

(60) Provisional application No. 60/437,104, filed on Dec. 30, 2002.

(51) Int. Cl.
*A61K 31/7076* (2006.01)
*A61K 31/708* (2006.01)
*A61N 1/05* (2006.01)

(52) U.S. Cl. ................. 514/45; 607/3; 607/50; 514/46

(58) Field of Classification Search ............ 514/42, 514/45, 263.1
See application file for complete search history.

(56) References Cited

U.S. PATENT DOCUMENTS

| 4,764,506 | A | 8/1988 | Patt |
| 4,912,092 | A | 3/1990 | Gruber |
| 4,919,140 | A * | 4/1990 | Borgens et al. ............... 607/50 |
| 5,008,251 | A | 4/1991 | Gruber |
| 5,447,939 | A | 9/1995 | Glasky |
| 5,672,588 | A | 9/1997 | Knutsen et al. |
| 5,958,933 | A * | 9/1999 | Naftchi .................... 514/263.2 |
| 6,027,936 | A | 2/2000 | Glasky |
| 6,060,459 | A | 5/2000 | Von Borstel et al. |
| 6,312,469 | B1 * | 11/2001 | Gielen et al. ............ 623/17.11 |
| 6,338,963 | B1 | 1/2002 | Glasky et al. |
| 6,440,455 | B1 | 8/2002 | Benowitz |
| 6,487,446 | B1 * | 11/2002 | Hill et al. ..................... 604/20 |
| 6,551,612 | B2 | 4/2003 | Benowitz |
| 2002/0055484 | A1 | 5/2002 | Benowitz |
| 2002/0137721 | A1 | 9/2002 | Benowitz |
| 2003/0055021 | A1 | 3/2003 | DeNinno |

FOREIGN PATENT DOCUMENTS

WO    WO01/08691    *    2/2001

* cited by examiner

*Primary Examiner*—Shaojia Anna Jiang
*Assistant Examiner*—Eric Olson
(74) *Attorney, Agent, or Firm*—Thomas A. Walsh; Homer W. Faucett, III; Ice Miller LLP

(57) ABSTRACT

Injuries to the central nervous system, particularly spinal cord injuries, are treated by administering a purine nucleoside or analog to the patient and, optionally, electrically stimulating the site of injury.

19 Claims, 3 Drawing Sheets

Skin Flap

A

Cutaneous Trunci Muscle Reflex

B  C  D  E

METHOD OF TREATMENT FOR SPINAL CORD INJURY

This application claims the benefit of U.S. Provisional Application Ser. No. 60/437,104, filed Dec. 30, 2002, which is incorporated by reference herein in its entirety.

BACKGROUND

Injuries to the central nervous system, including injuries to the spinal cord, are among the most devastating and disabling injuries possible. Depending upon the severity of the injury, paralysis of varying degrees can result. Paraplegia and quadriplegia often result from severe injury to the spinal cord. The resulting effect on the sufferer, be it man or animal, is severe. The sufferer can be reduced to a state of near immobility or worse. For humans, the mental trauma induced by such severe physical disability can be even more devastating than the physical disability itself.

In the mammalian central nervous system (CNS), nerve fibers begin to regenerate after injury or disease, but abruptly stop growing and do not form functional connections. This failure to form neural connections prevents the conduction of nerve impulses through the region of damage, which is the biological basis for the catastrophic behavioral loss after disease or injury to the CNS. A way to overcome this obstacle would be to provide some stimulus to induce significant nerve regeneration in the injured region. While this has been accomplished in limited circumstances in animals by the implantation of peripheral nerve bridges, the delivery of chemical growth factors, such as nerve growth factor (NGF) or brain derived neural growth factor (BDNF), or by the application of an electrical stimulus, each of these methods has serious shortcomings that limit or exclude use in humans. For example, there is no evidence that peripheral bridges actually modify the loss of behavior in animals. It also highly unlikely that surgeons will adopt the use of peripheral bridges, as the technique requires extensive surgery to the spinal cord or brain, risking additional damage. Further, the delivery of growth factors such as NGF and BDNF have been observed to have significant side effects, making patients extremely ill and/or stimulating the growth of latent tumors.

And, although the application of an electrical stimulus, using a technique such as oscillating field stimulation (OFS), has developed into a promising treatment for spinal cord injury, applied voltage also has shortcomings. The OFS procedure only works if the OFS stimulators are implanted within the first three weeks after injury in dogs and animals. It is very clear that the technique does not produce neural regeneration in chronically injured subjects. To date, OFS has failed to produce neural regeneration in over one hundred chronically injured (greater than two months post injury) laboratory guinea pigs (Borgens et al. (1993) *Restor Neurol and Neurosci* 5, 173–179). The inability to successfully treat chronic CNS injury poses a fundamental challenge, as there are estimated to be approximately 250,000–350,000 persons with longstanding spinal cord injuries.

Accordingly, methods for promoting neural regeneration in CNS injury, particularly in chronic CNS injury, are needed.

SUMMARY OF THE INVENTION

The present invention provides a method for the treatment of injuries to the central nervous system (CNS) in a patient, including injuries to the spinal cord. It has been found that a two-part therapy involving the application of electrical stimulation, such as oscillating field stimulation (OFS), in combination with the administration of a purine nucleoside, or analog thereof, such as inosine, produces nerve regeneration, resulting in at least a partial recovery of nerve functioning and behavior in patients suffering CNS injuries. The methods of the present invention are effective for the treatment of both acute and chronic injuries. Advantageously, the co-administration of a purine nucleoside, or analog thereof, such as inosine, extends the usefulness of OFS as a treatment option to chronic CNS injuries.

In one aspect, the present invention provides a method for treating a patient having a spinal cord injury, the method including electrically stimulating the site of the injury and administering a purine nucleoside or analog thereof to the patient, wherein nerve function through the injured spinal cord is at least partially restored and/or wherein nerve regeneration at the site of the spinal cord injury is stimulated. Electrical stimulation of the injury site may be accomplished by implanting a device into the patient. This device is preferably an oscillating field stimulation (OFS) device.

In another aspect, the present invention provides a method for treating a patient having a spinal cord injury by administering to the patient a purine nucleoside or analog thereof under conditions effective to stimulate nerve regeneration at the site of the injury and/or under conditions effective to at least partially restore nerve function through the injured spinal cord.

The spinal cord injury may be a complete severing of the spinal cord, a partial severing of the spinal cord, or a crushing or compression injury of the spinal cord. The spinal cord injury may have occurred more than three months prior to the treatment, more than three weeks prior to the treatment, or more than two weeks prior to the treatment.

Restoration of nerve function can be evidenced by restoration of nerve impulse conduction, a detectable increase in conduction action potentials, observation of anatomical continuity, restoration of more than one spinal root level, an increase in reflex behavior, or a combination thereof.

The purine nucleoside or analog thereof may be administered to the patient systemically, including orally or subcutaneously. The purine nucleoside or analog thereof may be administered locally to the site of the spinal cord injury. The purine nucleoside or analog thereof may be administered by implanting a device into the patient, which device administers the purine nucleoside or analog thereof. The purine nucleoside or analog thereof may be administered locally in a pharmaceutically acceptable carrier. A preferred purine nucleoside includes inosine.

Also included in the present invention is a kit for the treatment of a central nervous system (CNS) injury, the kit including, as a first component, a means for the application of an electrical stimulation to the injury site and, as a second component, a purine nucleoside or analog thereof. In some embodiments, the means for the application of an electrical stimulation to the injury site is an oscillating field stimulation (OFS) device. In some embodiments, the purine nucleoside or analog thereof includes inosine. In some embodiments, the kit further includes a device for the subcutaneous, intravenous, or intrathecal delivery of the purine nucleoside or analog thereof. In some embodiments, the kit further includes written instructions for the treatment of a CNS injury.

Definitions

As used herein, the term "patient" includes animals susceptible to CNS injuries, preferably mammals. In a preferred embodiment, the patient is a human. Other examples of patients include domestic pets, such as dogs and cats, or other mammals, such as goats and cows.

As used herein, the term "central nervous system" or "CNS" includes the nervous tissue of both the brain and spinal cord. The term does not include the peripheral nervous system (PNS). As used herein, the term "spinal cord" includes all neuronal structures of the spinal column.

Unless otherwise specified, "a," "an," "the," and "at least one" are used interchangeably and mean one or more than one.

BRIEF DESCRIPTION OF THE DRAWINGS

As shown in FIG. 1A, the afferent and efferent pathways of the CTM reflex are diagrammed on the left side of the guinea pig. On the right side of the guinea's pig spinal cord a spinal injury (a large gap for illustrative purposes) interrupts the ascending CTM tract on only that side. This produces a region on the back skin that no longer responds to tactile stimulation (it is areflexic). FIG. 1B shows the outline of an intact CTM receptive field. Tactile probing within this area produced twitching of the back skin, and outside of this region, stimulation did not produce CTM skin contractions. This series of light tactile stimulations of the skin of a sedated animal is videotaped from above and the drawings reconstructed by computer. FIG. 1C shows the results of a full-width spinal cord compression injury. The region outlined in the lower half of the CTM receptive field is the region of areflexia. It is this lower half of the CTM receptive field that no longer responds to tactile stimulation. FIG. 1D shows the outline of the region of CTM recovery. Within this region, CTM responsiveness has returned. FIG. 1E is a frame from the videotape showing the grid of dots tattooed on the animal's shaved back.

In FIG. 2A, the hole left after the removal of the marker is clearly visible, though the marker had shifted to near the right margin of the cord from its insertion in the midline. Still the plane of transection can be easily determined in even these cords since the scar and lack of axons to the left of the hole clearly establish the left margin of the transection plane. This is shown in FIG. 2B, another histological section where the marker has shifted to the right. The encircled region is a cyst full of macrophages shown in higher magnification in FIG. 2D. In FIG. 2C a marker hole in the center of the spinal cord (the margins are out of the field of view) is shown. Note to the left of the marker hole (in FIG. 2E) that long axons are present adjacent disorganized scar tissue, organized within undamaged parenchyma to the left of the right lateral hemisection. The plane of the section extends to the right margin of the cord, out of the field of view.

DETAILED DESCRIPTION OF ILLUSTRATIVE EMBODIMENTS

Figure 1:
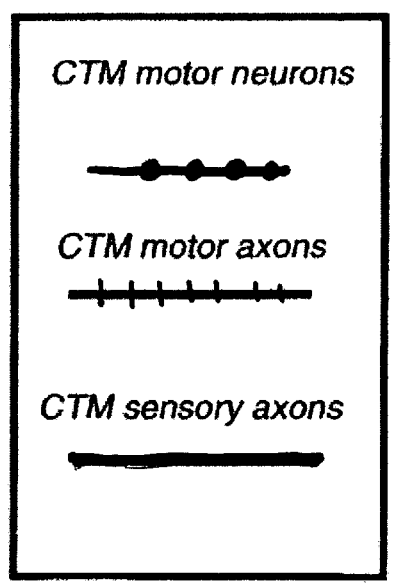
FIG. 1 represents the cutaneous trunci muscle (CTM) reflex as a behavioral index for spinal cord injury.
Figure 1:
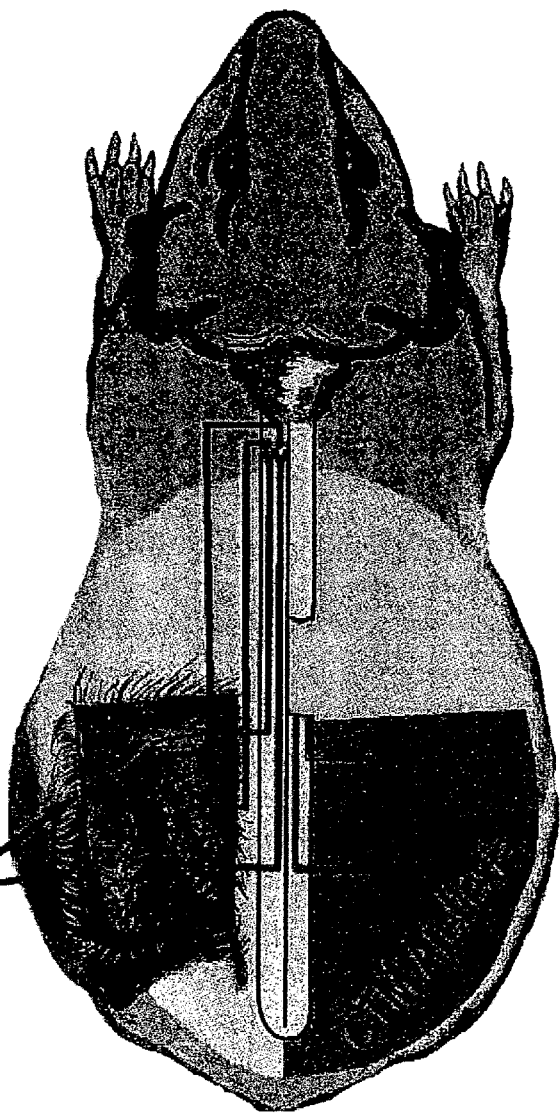
Figure 1:
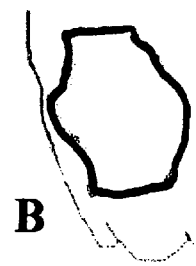
Figure 1:
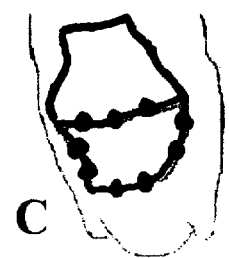
Figure 1:
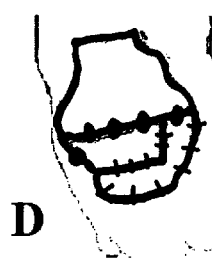
Figure 1:
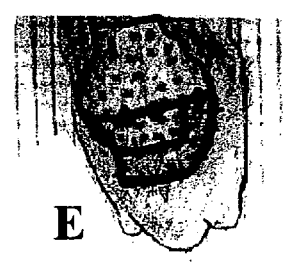

The present invention relates generally to methods for treating injuries to the mammalian central nervous system (CNS), including but not limited to spinal cord injuries, to at least partially restore nerve function. With the present invention, it has been found that a two-part therapy involving the application of electrical stimulation to the injured CNS in combination with the administration of a purine nucleoside or analog thereof produces nerve regeneration and restores nerve function in both acute and chronic CNS injuries. In a preferred embodiment, treatment of spinal cord injuries with the combined therapy of oscillating field stimulation (OFS) and the purine nucleoside inosine is used to produce spinal cord nerve regeneration and recovery of nerve functioning and behavior in spinal cord injuries in both acute and chronic spinal cord injuries.

A wide variety of injuries of the CNS may be treated by the methods of the present invention. As used herein, the term "injury" generally denotes a breakdown of the membrane of a nerve cell, such that there is a collapse in the ability of the nerve membrane to separate the salty gel on their insides (cytoplasm) from the salty fluid bathing them (extracellular fluid). The types of salts in these two fluid compartments are very different and the exchange of ions and water caused by injury leads to the inability of the nerve to produce and propagate nerve impulses—and further to the death of the cell. An injury includes damage that directly or indirectly affects the normal functioning of the CNS. The injury may be a structural, physical, or mechanical impairment and may be caused by physical impact, as in the case of a crushing, compression, or stretching of nerve fibers. Alternatively, the cell membrane may be destroyed by or degraded by an illness, a chemical imbalance, or a physiological malfunction such as anoxia (e.g., stroke), aneurysm, or reperfusion. A CNS injury includes, for example and without limitation, damage to retinal ganglion cells, a traumatic brain injury, a stroke-related injury, a cerebral aneurism-related injury, a spinal cord injury, including monoplegia, diplegia, paraplegia, hemiplegia and quadriplegia, a neuroproliferative disorder, or neuropathic pain syndrome.

With injury to the spinal cord of a mammal, connections between nerves in the spinal cord are broken. Such injuries block the flow of nerve impulses for the nerve tracts affected by the injury, with a resulting impairment to both sensory and motor function. Injuries to the spinal cord may arise from compression or other contusion of the spinal cord, or a crushing or severing of the spinal cord. A severing of the spinal cord, also referred to herein as a "transection," may be a complete severing or, may be an incomplete severing of the spinal cord.

The methods of the present invention may be used to treat both acute and chronic injuries of the CNS, including but not limited to acute and chronic spinal cord injuries. In preferred embodiments, the methods of the present invention are used to treat chronic injuries of the spinal cord. As used herein, the term "acute injury" includes injuries that have recently occurred. For example, an acute injury may have very recently occurred, may have occurred within an hour or less, may have occurred within a day or less, may have occurred within a week or less, or may have occurred within two weeks or less. As used herein, the term "chronic injury" is an injury that has persisted for a period of time. For example, a chronic injury may have occurred more than two weeks ago, may have occurred more than three weeks ago, may have occurred more than two months ago, or may have occurred more than three months ago.

One part of the two-part therapy for the treatment of CNS injuries of the present invention is the application of electrical stimulation to the site of the CNS injury. It has been known for two decades that electrical stimulation will enhance regeneration of mammalian spinal cord axons and reduce the retrograde degeneration of axons after an injury. Any of a variety of known methods of delivering electrical stimulation to the site of a CNS injury can be used. The method encompasses the application of a current through, and/or a voltage differential or potential across, the site of injury. The current can be an alternating or a direct current. The current and/or voltage differential can be constant or changing. Electrical stimulation of the CNS injury may be accomplished with the implantation of a bioelectric stimulator device.

A preferred method for electrically stimulating the site of injury is the use of oscillating field stimulation (OFS) wherein the polarity of an electric field is periodically reversed. Oscillating field stimulation has produced positive and beneficial results in the treatment of acute, severe, naturally produced paraplegia in dogs (U.S. Pat. No. 4,919,140), and is currently undergoing clinical trials for the treatment of acute spinal cord injuries in humans. However, all successful uses of such electrical stimulation to date have been limited to the treatment of acute injuries. Any regeneration of injured nerves in the CNS of mammals has been found to occur, if at all, only within a very short time period immediately after the injury occurs. After this short time period expires, nerves have not been found to regenerate. Thus, the present results for the effective treatment of chronic injuries are dramatic and unexpected.

Procedures for the implantation of a device (e.g., a "bioelectric implant") and the application of electrical stimulation to an injury site by OFS are well known in the art. A current is generated in order to produce a voltage differential or potential across the site of injury. A preferred bioelectric implant produces a standing direct current (DC) electrical field around the injury on the order of hundreds of $\mu V/mm$ (e.g. 100 $\mu V/mm$–500 $\mu V/mm$). In a small dog, this field can be generated by, for example, an approximately 200 $\mu A$ current running between two electrodes on either site of the injury. In a human, multiple pairs of electrodes are preferably used, as discussed below. The stimulator device is small and easily implanted surgically beneath the skin of the back. The amount of current needed to generate the weak electric field varies with the cross-sectional area of the injury site and the distance between the electrodes. It has been found that the use of 2 or more pairs of electrodes to deliver the requisite current is preferable as it reduces the amount of current passing through the intervening tissue. As the cross-sectional area increases, the number of electrode pairs used to create the field preferably also increases. For example, a 3-fold increase in cross-sectional area may require tripling of the number of electrodes in order to keep the amount of current passing through any tissue section at a safe level. For example, in one embodiment, six electrodes (3 pairs) are routed to the vertebral column and are affixed above and below the site of injury. The wires (electrodes) remain on the outside of the spine and do not touch the spinal cord itself—however the electrical field produced by them is imposed across the spinal cord. The entire unit is typically surgically removed approximately 14 weeks after implantation. This implantation/explantation has already been determined to be completely safe during Phase One trials in human spinal cord injured patients. See, for example, U.S. Pat. No. 4,919,140, Borgens et al. (1986) *J Comp Neurol* 250, 168–180; Borgens et al. (1987) *Science* 238, 366–369; Borgens et al. (1990) *J Comp Neurol* 296, 634–653; Borgens et al. (1993) *Restor Neurol Neurosci* 5, 305–322; Borgens et al. (1993) *Restor Neurol Neurosci* 5, 173–179; Borgens and Bohnert (1997) *Exp Neurol* 145, 376–89; Borgens et al. (1999) *J Neurotrauma* 16, 639–57; Borgens (1999) *Neuroscience* 91, 251–64; and Borgens (2003) *Restoring Function to the Injured Human Spinal Cord*, (Springer-Verlag, Heidelberg). The complete core circuitry and schematic of a representative bioelectric stimulator are as shown, for example, in Borgens et al. (1999) *J Neurotrauma* 16, 639–57. In the two part treatment of the invention, the electrical stimulation (administered via the "bioimplant") and the health food additive inosine or other purine nucleoside or analog thereof (administered orally or via subcutaneous injection) can be delivered, preferably concurrently, anytime post-injury.

The length of the time period for the application of electrical stimulation, such as OFS, to the injured site may vary. An electrical stimulation may be administered for several days, for example, for about one day, for about two days, for about three days, for about four days, for about five days, or for any interval thereof. An electrical stimulation may be administered for weeks, for example, for about one week, for about two weeks, for about three weeks, for about four weeks, or for any interval thereof. An electrical stimulation may be administered for several months, for example, for about one month, for about three months, for about four months, for about five months, for about six months, or for any interval thereof. For the treatment of an acute injury, the application of an electrical stimulation to the injured site may begun almost immediately after the injury has occurred, or the application of an electrical stimulation to the injured site may begin several hours or several days after the injury has occurred. For example, treatment may begin about 8 to about 12 hours post injury, several days post injury, or about 14 to about 21 days post injury. For the treatment of a chronic injury, the application of an electrical stimulation may begin at any point in time. For example, application may begin about two weeks after an injury, about three weeks or about one month after an injury, or may begin several months or several years after an injury.

The second part of the two-part therapy for the treatment of CNS injuries according to the present invention is the administration of a purine nucleoside or analog thereof. As used herein, "purine nucleoside" includes any purine base linked to a sugar, or an analog thereof. For example, purine nucleosides include guanine, inosine, or adenine and analogs thereof, include 6-thioguanine (6-TG) and the like. In a preferred embodiment, the purine nucleoside is inosine.

It has recently been demonstrated that the purine nucleosides, inosine and guanosine, act as neurotrophic agents, stimulating axonal outgrowth when administered in vitro to retinal ganglion cells (see U.S. Pat. No. 6,440,455 and Benowitz et al. (1999) *Proc Natl Acad Sci USA* 96, 13486–90). Inosine is a naturally occurring metabolite without known side effects. And, as demonstrated by the present invention, when administered in vivo, inosine acts as a "mild" nerve growth factor, without the serious side effects associated with the administration of more commonly known nerve growth factors, such as NGF. Purine nucleosides, and analogs thereof, for use in the present invention are readily available. For example, inosine is commercially available from chemical supply companies (including, for example, Sigma Chemical Company, St. Louis, Mo.) or health stores that sell health supplements.

It should be understood that the purine nucleoside or analog thereof can, according to the invention, be administered as part of the two-part therapy or, alternatively, as a therapy without concomitant electrical stimulation of the injury site. In the latter application, the CNS injury is preferably a spinal cord injury, which can be either an acute injury or a chronic injury.

The length of the time period for the administration of a purine nucleoside, or analog thereof, such as inosine, may vary. A purine nucleoside, or analog thereof, may be administered for several hours, for example, for about one hour, for about two hours, for about four hours, for about six hours, for about eight hours, or about twelve hours, or for any interval thereof. A purine nucleoside, or analog thereof, may be administered for several days, for example, for about one day, for about two days, for about three days, for about four days, for about five days, or for any interval thereof. A purine nucleoside, or analog thereof, may be administered for several weeks, for example, for about one week, for about two weeks, for about three weeks, for about four weeks, or for any interval thereof. A purine nucleoside, or analog thereof, may be administered for several months, for example, for about one month, for about three months, for about four months, for about five months, for about six months, or for any interval thereof. For the treatment of an acute injury, the administration of a purine nucleoside, or analog thereof, may begin almost immediately after the injury has occurred. Alternatively, the administration of a purine nucleoside, or analog thereof, may begin several hours or several days post injury. For example, treatment may begin about 1 to about 2 hours post injury, about 4 to about 6 hours post injury, about 2 days to about 6 days post injury, or about 14 days to about 21 days post injury. For the treatment of a chronic injury, the administration of a purine nucleoside, or analog thereof, may begin at any point in time. For example, administration may begin about two weeks after an injury, may begin about three weeks or about one month after an injury, or may begin several months or several years after an injury.

In the methods of the present invention, a purine nucleoside, or analog thereof, may be provided in a pharmaceutically acceptable carrier. As used herein, the term "pharmaceutically acceptable carrier" includes any and all solvents, dispersion media, coatings, antibacterial and anti fungal agents, isotonic and absorption delaying agents, and the like that are physiologically compatible. Such carriers include, for example, water, preferably sterile and including distilled water, and any other pharmaceutically acceptable carrier known to the art that will not have an adverse effect on the treatment. In some embodiments, a preferred carrier for inosine is sterile lactated Ringers.

In another aspect of the invention, the purine nucleoside, or analog thereof, may be administered in a pharmaceutically acceptable formulation. The pharmaceutically acceptable formulation may be a dispersion system, for example, a lipid-based formulation, a liposome formulation, a multivesicular liposome formulation, nanocapsules, microspheres, beads, or a lipid-based formulation, including oil-in-water emulsions, micelles, mixed micelles, synthetic membrane vesicles, and resealed erythrocytes. The pharmaceutically acceptable formulation can also comprise a polymeric matrix, selected, for example, from synthetic polymers such as polyesters (PLA, PLGA), polyethylene glycol, poloxomers, polyanhydrides, and pluronics or selected from naturally derived polymers, such as albumin, alginate, cellulose derivatives, collagen, fibrin, gelatin, and polysaccharides.

In yet another aspect of the invention, the pharmaceutically acceptable formulation provides sustained delivery or "slow release" of the purine nucleoside to a subject for at least one, two, three, or four weeks after the pharmaceutically acceptable formulation is administered to the subject. Sustained delivery of a formulation of the invention may be provided by use of, for example, slow release capsules, or an infusion pump.

The precise amount of a purine nucleoside, or analog thereof, used in any one embodiment of the present invention will vary according to factors known in the art including but not limited to the physical and chemical nature of the purine nucleoside, or analog thereof, the nature of the pharmaceutically acceptable carrier, the intended dosing regimen, the state of the subject's injury, and the method of administering the purine nucleoside, or analog thereof. Accordingly, it is not practical to set forth generally the amount that constitutes an amount of a purine nucleoside, or analog thereof, effective for all possible applications. Those of ordinary skill in the art, however, can readily determine the appropriate amount with due consideration of such factors. A non-limiting range for a therapeutically effective concentration of inosine is about 1 µM to about 100 mM, more preferably about 50 µM to about 50 mM. A non-limiting range for a therapeutically effective concentration of guanosine is about 1 µM to about 100 mM, more preferably about 50 µM to about 50 mM.

With the present invention, a purine nucleoside, or analog thereof, may be administered to a subject by a wide variety of means. A purine nucleoside, or analog thereof, may be administered systemically to a subject in need of treatment for a CNS injury. For example, a purine nucleoside, or analog thereof, may be administered intravenously through the blood supply, subcutaneously, intraperitoneally, transdermally, or orally. For subcutaneous delivery, an infusion pump or minipump may be used. Likewise, a purine nucleoside, or analog thereof, may be administered locally to the site of CNS injury. For example, a purine nucleoside, or analog thereof may be delivered intrathecally, into the sheath of the spinal column. An infusion pump or minipump may be used for such local delivery.

For treatment of a CNS injury, both the electrical stimulation of the injured site and the administration of a purine nucleoside, or analog thereof, may be started at the same point in time. Alternatively, one part of the two part therapy of the present invention may be started before the other. That is, the electrical stimulation of the injured site may be initiated before the administration of a purine nucleoside, or analog thereof, or, the administration of a purine nucleoside, or analog thereof, may be initiated before the electrical stimulation of the injured site. In other words, electrical stimulation of the injured site and the administration of a purine nucleoside or analog thereof may be begun and/or halted at the same or different points in time.

Alternatively, one part of the two part therapy of the present invention may be completed before the other. That is, the electrical stimulation of the injured site may be stopped before the administration of a purine nucleoside, or analog thereof, is stopped, or, the administration of a purine nucleoside, or analog thereof, may be stopped before the electrical stimulation of the injured site is stopped.

Preferably there is a period during the treatment period where both electrical stimulation of the injury site and administration of the purine nucleoside or analog thereof are administered simultaneously or concurrently. However, it should be noted that the invention also encompasses sequential administration of the electrical stimulation of the injured site and the administration of a purine nucleoside, or analog thereof. In a sequential administration, the period in between the two parts of the treatment is preferably short, e.g., less than hours or days. Likewise the invention encompasses alternating or intermittent administration of the electrical stimulation and the purine nucleoside or analog thereof. In other words, the invention is not intended to be limited by the order in which the two therapies are administered or whether they are administered in a strictly simultaneous fashion. While concurrent administration of the electrical stimulation and the purine nucleoside or analog thereof is preferable, it is envisioned at a minimum both therapies are part of a coordinated treatment plan.

The methods of the present invention are effective for at least partial restoration of nerve function and/or nerve regeneration following a CNS injury. The efficacy of the treatment of the present invention may be determined in a variety of ways. For example, the efficacy of the treatment of the present invention may be determined by methods that detect restoration of nerve function. Restoration or increase in conduction of action potentials, such as CAPs, through the injured site may be used as an indicator that nerve function has at least partially been restored. Nerve function is considered to have been at least partially restored if there is an increase in the conduction of action potentials after treatment. Preferably, the treatment will be conducted sufficiently to achieve at least about 10% increase in conduction of CAPs. Moreover, restoration of anatomical continuity may also be observed by examination with high-resolution light microscopy and/or by diffusion of intracellular fluorescent dyes through the repaired nervous tissue, such as repaired axons, or by direct observation of repaired axonal membranes, as described in the examples. Additionally, in human applications, the efficacy of preferred treatments may be observed by the restoration of more than one spinal root level as determined by the American Spinal Injury Association (ASIA) motor score and/or the National Animal Spinal Cord Injury Study (NASCIS) score as know in the art and as described in Wagih et al. (1996) *Spine* 21, 614–619. Furthermore, in veterinary applications, behavioral analysis of the cutaneous trunci muscle (CTM) reflex, as more fully discussed in the examples, may also be used to determine the efficacy of the treatment, and whether nerve function has at least partially been restored. Using this analysis, nerve function is considered to have been at least partially restored if there is an increased reflex behavior after treatment, but treatments are desirably preferred so as to achieve at least about a 10% increase in the area of CTM behavioral recovery. The efficacy of the method of treatment of the present invention may also be determined by a combination of the above-discussed methods.

The efficacy of the treatment of the present invention may be determined by methods that detect nerve regeneration. For example, nerve regeneration may be observed by examination with high-resolution light microscopy and/or by diffusion of intracellular fluorescent dyes through the repaired nervous tissue, such as repaired axons, or by direct observation of repaired axonal membranes, as described in the examples.

In some embodiments, electrically stimulating the site of the CNS injury and administering a purine nucleoside, or analog thereof, to the patient may result in an increase in the restoration of nerve function that is greater than that obtained with electrically stimulating the site of the CNS injury alone or administering a purine nucleoside, or analog thereof, alone. In some embodiments, electrically stimulating the site of the CNS injury and administering a purine nucleoside, or analog thereof, to the patient may result in a synergistic increase in the restoration of nerve function. That is, the restoration in nerve function obtained with the two part therapy is greater than the sum of the restoration in nerve functions obtained with electrically stimulating the site of the CNS injury alone and administering a purine nucleoside, or analog thereof, alone.

In some embodiments, the present invention may include, in addition to the treatment of an injury with the application of an electrical stimulation and the administration of a purine nucleoside, or analog thereof, the treatment of the injury with other conventional management compounds and/or compositions. For example, the injury may also be treated with a polyalkylene glycol or a steroid, such as methylprednisolone. For example, a polyalkylene glycol may be administered as described in WO 02/092,107 and U.S. patent application Ser. No. 09/438,206, filed Nov. 12, 1999.

Also contemplated within the scope of the present invention is the treatment of a CNS injury by the administration of a purine nucleoside, or analog thereof, without the application of electrical stimulation to the injury site. For example, a spinal cord injury, including, but not limited to a chronic spinal cord injury, may be treated by the administration of inosine, without the application of an electrical stimulation.

The present invention provides a kit for treating a CNS injury, including, but not limited to a spinal cord injury. The kit will typically include a first component and a second component in a suitable packaging material. The first component is a means of administering an electrical stimulation to the site of injury, such as, for example, an OFS device. The second component is a purine nucleoside, or analog thereof, in an amount sufficient for treatment. The purine nucleoside, or analog thereof, may be in a pharmaceutical formulation appropriate for subcutaneous, intravenous, intrathecal, local delivery, or the like. The purine nucleoside, or analog thereof, may be inosine. Additionally, the kit may include other reagents, such as buffers and solutions, needed to practice the invention. Instructions for administering an electrical stimulation and/or administering a purine nucleoside, or analog thereof, for the treatment of a CNS injury are also typically included. The kit may further include additional devices or reagents necessary, for example, for the subcutaneous, intrathecal, or intravenous delivery of a purine nucleoside, or analog thereof. Such devices or reagents may include, for example, minipumps, syringes, needles, local anesthetics, and the like. As used herein, the term "packaging material" refers to one or more physical structures used to house the contents of the kit. The packaging material is constructed by well-known methods, preferably to provide a sterile, contaminant-free environment. The packaging material has a label that indicates that the first component and second component can be used for the treatment of a CNS injury. As used herein, the term "package" refers to a solid matrix or material such as glass, plastic, paper, foil, and the like. "Instructions for use" typically includes a tangible expression describing the preparation and administration of the first and/or second components of the kit for the treatment of a CNS injury.

The present invention is illustrated by the following examples. It is to be understood that the particular examples, materials, amounts, and procedures are to be interpreted broadly in accordance with the scope and spirit of the invention as set forth herein.

EXAMPLES

Example 1

Behavioral and Anatomical Synergism by Simultaneous Application of Two Neurotrophic Factors: Applied Gradients of Extracellular Voltage and Inosine With this example, a combination treatment of oscillating field stimulation (OFS) and inosine infusion was used to enhance functional responses after spinal cord injury (SCI). Chronic cutaneous trunci muscle (CTM) functional deficits in the adult guinea pig were chosen for study as the SCI behavioral model for several reasons. First, transection of the relevant ascending CTM white matter tracts produces permanent loss of CTM functions for the life of the animal. And, although the behavioral deficits have been partially reversed by application of electrical fields during the acute stage of the injury in both guinea pigs and clinical cases of paraplegia in dogs (Borgens et al. (1990) *J. Comp. Neurol.* 296, 634–653; Borgens et al. (1993) *Restor Neurol Neurosci* 5, 173–179; Borgens (1999) *Neuroscience* 91, 251–64)), recovery of function has not been improved in response to treatments made to older, chronic injuries. In particular, in over one hundred attempts, a spontaneous recovery of CTM functioning after SCI or recovery in response to the application of electrical fields has never been observed for CTM lesions greater than 2 months old in the adult guinea pig (Borgens et al., (1993) *Restor Neurol Neurosci* 5, 305–322).

This example reports, for the first time, that such chronic CTM deficits can be partially reversed by treatment with either inosine alone or inosine combined with OFS. Further, treatment with inosine in combination with OFS produced a more robust recovery than with either OFS or inosine alone.

This study was composed of two parts, Study One and Study Two. The main investigation, Study One, was an anatomical and behavioral evaluation of recovery from chronic SCI in adult guinea pig in response to the application of inosine and OFS. Study Two evaluated anatomical responses only of transected white matter to the acute application of inosine and OFS in adult guinea pig SCI. The following Methods apply to both studies, except where noted.

Animals, Anesthesia, and Surgery

Fully adult (approximately 400 grams (g)) female guinea pigs were used in this study (Hartley Strain). They were anesthetized with ketamine/xylyzine by conventional methods (Borgens et al. (2002) *J. Exp. Biol.* 205, 1–12) prior to surgery, kept warm with heat lamps after surgery, and maintained individually in pens and fed ad libidum for the duration of the investigation. Animals were euthanized at the end of the study, prior to the harvesting of spinal cords for anatomical study by an overdose of the anesthesia (see Borgens et al. (2002) *J. Exp. Biol.* 205, 1–12).

A laminectomy procedure exposing the dorsal aspect of the spinal cord was performed on all animals between T9 and T11. A right lateral hemisection was performed (FIG. 1) using a special cutting device, and further confirmed to be "complete" (that is, leaving no spared parenchyma) by passing a sharpened pin through the cut tissue. This operation severs the entire right side of the cord from the midline to the far right border of the spinal cord forming a rostral and caudal segment. The entire left side of the spinal cord was left intact. Immediately after transection, a marker device made of surgical stainless steel was inserted into the lesion, as previously described in Borgens et al. (1986) *J. Comp. Neurol* 250, 168–180 and Borgens and Bohnert (1997) *Exp. Neurol.* 145, 376–389. This device was left in situ for the duration of the study, and removed prior to histological processing. This procedure leaves a hole in the tissue, which accurately marks the exact plane of transection even in chronic injuries many months old (FIGS. 1 and 2).

Figure 2:
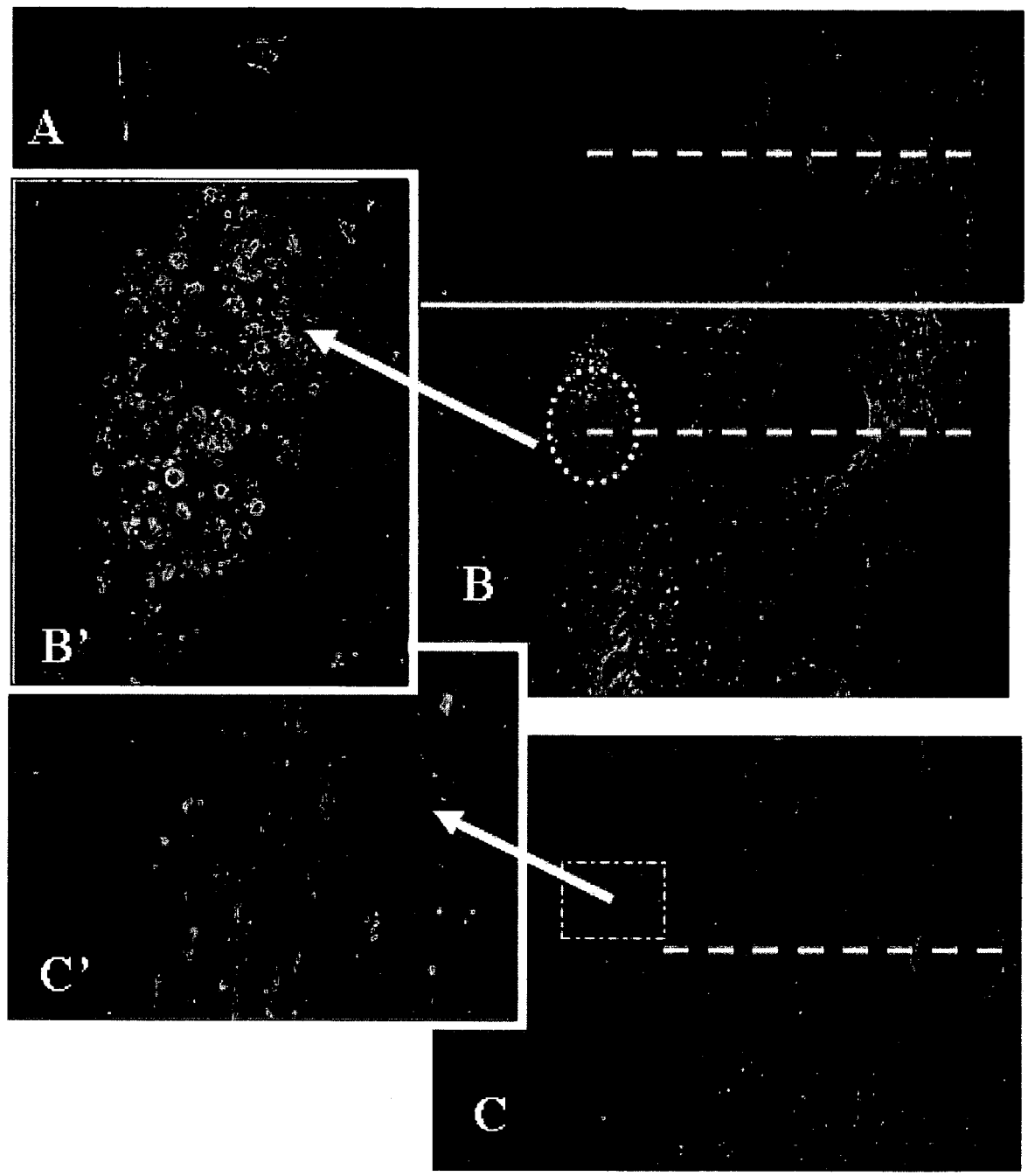
FIG. 2 represents the histological determination of the plane of transection using an indwelling marker device. In all photomicrographs of the spinal cord, the cord is oriented with its long axis from top to bottom of each photograph. "Top" is the head end (Rostral), while the caudal (tail end) is toward the bottom. Both margins of the spinal cord can be seen in photomontage FIG. 2A, while only the right margin can be seen in FIG. 2B. The hatched line represents the exact plane of transection established by the marker.

As shown in FIG. 1A, the afferent and efferent pathways of the CTM reflex are diagrammed on the left side of the guinea pig. Nociceptive receptors in the skin project sensory afferents into the spinal cord via the dorsal cutaneous nerves (DCNs). DCNs are segmentally arranged roughly parallel to each other, are perpendicular to the spinal cord, and project into the spinal cord as a component of the dorsal roots. The ascending CTM afferents project up the spinal cord as a tract. The CTM tract is located just lateral to the spinothalamic tract in the ventral funiculus on both right and left sides. Very few relays make up the ascending tract, which projects onto a pool of motor neurons located at the cervical/thoracic junction. These in turn project efferent motor fibers back to the cutaneous trunci muscle of the skin via the lateral thoracic branch of the brachial plexus. A neural connection between left and right neuron pools does not exist, though there is minor contralateral innervation within the spinal cord's ascending CTM projections. On the right side of the guinea's pig spinal cord a spinal injury (a large gap for illustrative purposes) interrupts the ascending CTM tract on only that side. This produces a region on the back skin that no longer responds to tactile stimulation (it is areflexic). This region of areflexia is ipsalateral and below the level of this right lateral hemisection of the spinal cord. Note that the CTM reflex ipsilateral and above, and contralateral to, the injury is not affected. A full-width injury compromising both CTM tracts would eliminate skin responsiveness on both sides of the animal below the lesion. The back skin rostral to the injury would be unaffected by this spinal cord injury. This is shown in the video reconstructions presented in FIG. 1. FIG. 1B shows the outline of an intact CTM receptive field. Tactile probing within this area produced twitching of the back skin, and outside of this region, stimulation did not produce CTM skin contractions. This series of light tactile stimulations of the skin of a sedated animal is videotaped from above and the drawings reconstructed by computer. FIG. 1C shows the results of a full-width spinal cord compression injury. The region outlined in the lower half of the CTM receptive field is the region of areflexia. It is this lower half of the CTM receptive field that no longer responds to tactile stimulation. FIG. 1D shows the outline of the region of CTM recovery. Within this region, CTM responsiveness has returned. FIG. 1E is a frame from the videotape showing the grid of dots tattooed on the animal's shaved back. This grid is useful for further quantification of the CTM reflex, combined with the outlines drawn on the animal's back with markers during CTM testing.

All study groups were evaluated for another 3 months until sacrifice.

For Study One, the transaction of the cord was performed and the animals remained untreated for approximately 3 months. Experimental treatments were then performed on the chronic animals, as outlined below.

In Study Two, animals were transected and treated experimentally within 24 hours. Spinal cords were injected with intracellular axonal markers approximately 30 days post-transection, and harvested approximately 18 hours later, after euthanasia. Only anatomical evaluation was performed on the animals of Study 2. Behavioral tests were not performed.

Experimental Groups

In Study One, the three experimental groups were as follows:

1) An "Inosine Only" group. Fifteen animals were subcutaneously implanted with a Alzet micro-osmotic pump (model number 1002) under the back skin of the neck region. This pump delivered 0.25 milliliter (mL)/hour of an inosine solution (10 millimolar (mM) in sterile lactated ringers). The continuous infusion of inosine continued for 14 days and was then discontinued until euthanasia and sacrifice, approximately 2½ months later.

2) An "Inosine and OFS" group. These sixteen animals received the identical infusion of inosine as described above, but in addition were implanted at the same time with a miniaturized OFS unit (Moriarty and Borgens (1999) *Restor Neurol Neurosci* 14, 53–64). The miniaturized OFS unit delivered approximately 45 milliamps (mA) total current for 4 weeks, with a reversal of polarity set at 15 minutes duty cycle (see Stimulator Design and Implantation, below).

3) A "Control" group of fifteen animals. These animals were implanted with an Alzet pump that delivered only sterile lactated ringers and a sham OFS stimulator that did not function.

All animals in Study One were subjected to CTM behavioral evaluation and anatomical evaluation of white matter at the end of this component of the study.

Study One did not include Sham or Active OFS Implant Alone study groups in this investigation. Rather, as significant numbers of similarly treated chronic guinea pigs have been treated in previous experiments using both Active and Sham OFS stimulator implantation, and these data have been reported elsewhere (Borgens et al. (1993) *Restor Neurol Neurosci* 5, 305–322), this historical data is used here. Briefly, as reported in more detail in Borgens et al. (1993) *Res Neurol & Neurosci* 5, 173–179, of twenty-six animals implanted with sham stimulators at three months post hemisection, twenty-one were observed for more than twelve months following hemisection, one for six months, and three for less than six months. In all animals, the region of areflexia was not observed to change in terms of character, size, or side of flank throughout the duration of observation. A complete lack of CTM reflex activity in response to tactile stimulation within the region of areflexia was characteristic of all sham-treated animals. In animals implanted with active electrical stimulators at three months post hemisection, no recovery of CTM reflex was observed in thirteen animals with rostally applied negative field, eight of which were followed for at least nine months, five of which were observed for three months; or in eleven animals with caudally negative applied field, eight of which were observed for nine months and three of which were observed for three months. As in the sham treated group, the area of areflexia in the electrically treated animals was unchanged in form and character for the duration of the study.

In Study Two, an "Inosine Only" group (fourteen animals), an "Inosine and OFS" group (fifteen animals), and a "Control" group (thirteen animals) were evaluated at the end of approximately sixty days using only anatomical methods.

Behavioral Evaluation of the CTM reflex after SCI

A behavioral model of choice for evaluation on long tract sensorimotor functioning after SCI is the CTM Reflex (Blight et al. (1990) *J of Comp Neurol* 296, 614–33; reviewed in Borgens (2003) *Restoring Function to the Injured Human Spinal Cord* (Springer-Verlag, Heidelberg)). The CTM reflex is observed as a muscular contraction of the skin and observed as a "rippling" in response to local tactile stimulation of the flank skin. The CTM reflex in the context of spinal cord injury, as well as its neurological circuit, which has been completely identified in both rats (Theriault and Diamond (1988) *J Neurophysiol* 60, 446–462) and guinea pigs (Blight et al. (1990) *J of Comp Neurol* 296, 614–33) is well known in the art. Voluntary "walking and stepping" models of SCI in laboratory rats and guinea pigs were not used in the present studies because of the high probability of spinal (reflexive) walking and stepping, after even complete transection, and the fact that the neural circuit underlying voluntary locomotion has not been sufficiently identified (Blight et al. (1990) *J of Comp Neurol* 296, 614–33; Borgens et al. (2002) *J. Exp. Biol.* 205, 1–12; Borgens (2003) *Restoring Function to the Injured Human Spinal Cord* (Springer-Verlag, Heidelberg)). An important characteristic of the CTM reflex model is that a total and complete loss of CTM functioning after transaction of the ascending afferent tract within the spinal cord. This does not recover spontaneously (in any degree) for the life of the animal (Blight et al. (1990) *J of Comp Neurol* 296, 614–33; Borgens (2003) *Restoring Function to the Injured Human Spinal Cord.* (Springer-Verlag, Heidelberg)). In this particular study, all of the muscular contraction(s) of the back skin ipsilateral to (on the right side), and below, the transaction would not be expected to ever function again in untreated animals.

A complete description of the means to describe, assay, and quantify CTM behavior is found, for example, in Borgens et al. (2002) *J. Exp. Biol.* 205, 1–12. Briefly, a matrix of dots is marked on the shaved back skin of the guinea pig. When the skin contracts (usually in the direction of the local stimulus) the dots move as well. The entire sequence of stimulation of the back skin with a monofilament probe eliciting CTM movement is videotaped from above (FIG. 1). This is performed on the intact (uninjured animal) prior to SCI to establish an individual pattern of CTM movement for each individual animal.

Using a dry erase marker, the technician marks the boundary of responding and non-responding skin in the intact animal providing a complete picture of the total receptive field of the CTM on the animal's back skin. Loss of the CTM reflex is observed as a region of skin that no longer responds to tactile stimulation, and a recovery of the CTM reflex is defined as a return of skin contraction in response to light tactile stimulation in this region. While the vector, contraction speed, and latency of CTM responses subsequent to stimulation can be derived from quantitative computer managed evaluation of the videotaped behavior (Borgens et al. (2002) *J. Exp. Biol.* 205, 1–12), the most informative measure is the Percent Area of Loss of the CTM relative to the originally intact receptive field. For example, if the cord were completely transected from left to right in the mid thoracic region, about 50% of the total receptive field would be expected to be destroyed. This is because the receptive fields above the plane of transection are completely intact and functioning. Thus, 50% of CTM responsiveness is lost "below" (caudal to) the lesion, and 50% remains intact "above" (rostral to) the lesion.

In the transection procedure used in the present example (a right unilateral hemisection), the cord is completely transected on only one side of the midline, thus CTM functioning is normal both "above" the plane of the lesion and on the "contralateral" side. This usually produces a loss of CTM responsiveness of about 25% of the total receptive field.

Intracellular Labeling of the Axons of Spinal Cord White Matter

The injection of various intracellular labels into guinea pig spinal cord white matter has been described in numerous previous publications. See, for example, Borgens et al. (1986) *J Comp Neurol* 250, 168–180 and Borgens et al. (1999) *Journal of Neurotrauma* 16, 639–57. Briefly, approximately 18 hours prior to the sacrifice of the animal, the spinal cord was exposed by surgery, and approximately 20 mL of a fluorescently labeled dextran was injected using a Hamiliton syringe. The label (50% in distilled water; 10,000 Daltons) was injected deep into the parenchyma of white matter, approximately two vertebral segments rostral and caudal of the plane of transection (usually still visible, due to the indwelling marker device). A FITC conjugated dextran ("Flouro-emerald") was injected rostral to the plane of transection, and a rhodamine-conjugated dextran ("Flouro-ruby") was injected caudal to the plane of transaction. Thus, this anterograde double label technique marked both ascending fibers (mostly sensory afferent fibers) projecting towards the lesion from below it and descending axons (mainly motor fibers) projecting towards the lesion from above it). Longitudinal horizontal sections provided histological samples in which the entire extent of projection of a single axon often can be traced to fall short of, or regenerate to, around, or through the plane of transection.

This procedure can sometimes provide dramatic examples of single unit axon degeneration and regeneration. However, it is not productive to attempt to count individual axons in longitudinal horizontal sections. Often axons take tortuous and curving trajectories, and would be counted more than once in individual histological samples. Additionally, sprouting and branching of fibers can lead to false counting relative to the extended growth from the stump of an individual severed fiber. Rather, the proportion of animals in which axons can be traced to terminate more than 250 µms from the plane of transaction (exactly identified by use of the indwelling marker), within 250 µms of the actual plane of transaction, and to cross the exact plane of transection into the adjacent segment of cord is compared. The evaluator was unaware of the animal's experimental treatment when obtaining these data. Images from an Olympus Van Ox microscope were obtained with an Optronics DEI-750 color video camera and captured to a PC with Adobe Twain 32 software.

Stimulator Design and Implantation

The miniaturized OFS units implanted into guinea pigs were identical to those used in previously published reports (Moriarty and Borgens (1999) *Restor Neurol Neurosci* 14, 53–64). Fabrication and schematic circuits of OFS implants are known in the art (Borgens et al. (1993) *Restor Neurol Neurosci* 5, 305–322; Borgens (1999) *Neuroscience* 91, 251–64). Briefly, individual units were coated with a medical grade Teflon, their output was 30 µA total DC current, with a reversal of polarity occurring every 15 minutes. The long pair of Teflon-coated stimulator leads were surgically routed from the site of stimulator implantation (under the back-skin) to the vertebral column where they were fastened to paravertebral musculature. The uninsulated ends of these platinum/iridium medical grade electrodes were located rostral and caudal of the spinal lesion by about two vertebral segments. It is estimated that these units produced an effective current density of 45 $\mu A/cm^2$ associated with a field strength of approximately 10 mV/mm. These estimates are based on quadrapole measurements of current density and field strength during stimulation (Borgens et al. (1990) *J. Comp. Neurol.* 296, 634–653).

Statistical Evaluation. Nonparametric evaluation and comparison of means usually involved the use of either Mann-Whitney or Wilcoxian tests, while the comparison of proportions was performed using Fishers' exact test, a more conservative variation of Chi Square testing. All comparisons were performed on Instat Software.

General Conduct of the Study

Long-term survival and health of animals in the chronically injured animals in Study One had originally been a concern, given the substantial surgery and implantation procedures for two devices (the OFS unit and the osmopump) and the long survival time required (6 months) after the original spinal cord surgery. However, of the 46 animals that entered Study One, only seven were required to be replaced for various difficulties. Two animals were removed after surgery, but before the experimental "treatment" began at approximately three months. They were removed because of evidence of a "missed" lesion, i.e. the CTM behavior was not abolished by spinal cord injury. One animal died immediately after the initial surgery. Three animals were removed prior to the experimental treatment because of problems of autophagy. One animal was replaced after the beginning of the experimental treatment due to a persistent infection at the site of device implantation. This was localized to the site of the OFS implant, and this animal was humanely euthanized and was never evaluated behaviorally or anatomically.

At the end of the investigation, the extent of the CTM loss was analysed by planimitry. The unit area of intact CTM receptive fields in each animal (tallied as 100%) was compared to the percent loss the following day after hemisection. This would establish if all groups received a similar standardized injury relative to the unit area of CTM deficits. All groups survived the surgery with a statistically similar CTM loss.

Behavioral Recovery of the CTM Reflex

Of the fifteen control animals that were implanted with a pump (delivering sterile saline only) and an inactive OFS unit, not one animal recovered any of the nonfunctional CTM receptive field. The character of their CTM responsiveness at the end of the study was identical to that produced by spinal cord hemisection, that is, approximately 25% of the receptive fields remained inactive. Varying amounts of recovery of the CTM was observed in both experimental groups; "Inosine Alone" and "Inosine Plus OFS." More animals recovered some amount of CTM behavior in the inosine treated group (11 animals) than in the combination treatment (6 animals); though this difference was not statistically significant (P=0.16; Fishers' exact test). Both treatments, however, produced a statistically significant recovery of the CTM reflex compared to the Control Group ("Control" vs. "Inosine Alone;" P<0.0001; "Control" vs. "Inosine Plus OFS;" 0.01, Fishers exact test). In the combination treatment, all but one of the recovering animals revealed an emerging CTM by one month after the experimental application. The recovery of the CTM was more delayed in response to the combination therapy (since only three of the eleven "Inosine Plus OFS" animals recovered during this same period post application). Even given that the total numbers of recovered animals in both groups was low, this difference was statistically significant (P=0.04; Fisher's exact test).

At the end of the study, the percent recovery of the CTM receptive field in response to the combination treatment was more variable, but greater than that achieved by the insosine treatment alone (mean of 28.1±17.8 compared to 23.5±3.6) however, this difference was not statistically significant (P=0.5; Mann Whitney).

The Anatomy of Axonal Regeneration

Table 1, below, provides the numbers of spinal cords that were injected with the intracellular label (N) and those that were lost to histology (LTH) for each of the three groups. The proportions of those cords in which marked fibers were traced to the four zones are given over the number of cords examined. Statistical Comparison between the groups is provided at the bottom of the graph (Fishers' exact two tailed test). This data is given for both rhodamine labeled Ascending fibers and FITC labeled Descending projections. Note that the number of cords lost to histology was not significantly different between any of the groups.

TABLE 1

|  | N | LTH | Zone 1 >250 | Zone 2 <250 | Zone 3 | Zone 4 |
|---|---|---|---|---|---|---|
| Ascending |  |  |  |  |  |  |
| 1. Control | 15 | 5 | 10 | 3/10 | 0/10 | 0/10 |
| 2. Inosine | 15 | 3 | 12 | 10/12 | 7/12 | 2/12 |
| 3. Inosine/OFS | 16 | 7 | 9 | 7/9 | 8/9 | 6/9 |
| Statistics |  |  |  |  |  |  |
| 1 vs. 2 |  |  | 0.68 | 0.03 | 0.005 | 0.48 |
| 1 vs. 3 |  |  | 0.71 | 0.07 | 0.0001 | 0.003 |
| 2 vs. 3 |  |  | 0.23 | 1.0 | 0.18 | 0.03 |
| Descending |  |  |  |  |  |  |
| 1. Control | 15 | 6 | 9 | 2/9 | 1/9 | 0/9 |
| 2. Inosine | 15 | 7 | 8 | 7/8 | 2/8 | 1/8 |
| 3. Inosine/OFS | 16 | 5 | 11 | 10/11 | 9/11 | 5/11 |
| Statistics |  |  |  |  |  |  |
| 1 vs. 2 |  |  | 1.0 | 0.02 | 0.58 | 0.47 |
| 1 vs. 3 |  |  | 0.7 | 0.004 | 0.005 | 0.04 |
| 2 vs. 3 |  |  | 0.47 | 1.0 | 0.02 | 0.17 |

Table 1 summarizes the results of anterograde filling of both ascending and descending tracts within the spinal cords of all animals in the Study One, of chronically injured animals. Note that not all spinal cords were deemed worthy of comparison. The most significant problem in those not compared or discussed here was poor uptake of label. Such "missed fills" were simple to delineate as acceptable cords showed fiber tracts that took up the dye two vertebral sections from the lesion on the left side of the spinal cord (untransected side). These usually projected often more than 1 centimeter past the hemisection. Thus spinal cords were not evaluated if they showed unmistakable signs of insufficient dye uptake or were otherwise poor candidates due to other problems in histological processing. In other words, only spinal cords that revealed intact and labeled axons within the spinal cord left of the midline, i.e. adjacent the hemisection, were anatomically evaluated (refer to FIG. 2). Only one other protocol was followed when determining the extent or distance of axonal projections relative to the lesion. The termination of axons was defined as a blunt or sometimes pointed tip when sharply in focus. Fibers were not considered to have terminated if the tip was not distinct, usually due to a declining intensity of fluorescence. Sometimes a false impression of an axon terminal may occur when a fiber is transected with the microtome (the remaining portion contained in the next histological section (see Borgens et al. (1986) *J Comp Neurol* 250, 168–180). However, this should not occur more often in a particular group, and the sections were evaluated and scored without knowledge of their experimental treatment.

Between 30% and 40% of the spinal cords in any one group suffered insufficient uptake of label (and/or other problems due to histological processing) to be useful. When the numbers of spinal cords that were lost to histology were compared between groups—including a comparison between the quality of rostral and caudal fills (descending tracts and ascending tracts respectively), there was no significant difference between them (Table 1). Finally, there was no evidence of dye uptake by dorsal roots between the point of dextran injection and the lesion and therefore there were no exclusions based on this (see Borgens and Bohnert (1997) *Exp Neurol* 145, 376–89).

In all but three control animals, anterogradely labeled fibers terminated at distances greater than 250 μm rostral or caudal to the plane of transection. In only one of these three (an ascending axon), the fiber was traced from the fill point (caudal to the lesion) to the plane of the lesion, but did not cross it. In the same animal, fibers projecting from the rostral cord did not reach this plane, but fell within approximately 100 μm of it. In the other two animals, anterogradely filled ascending and descending fibers crossed the 250 μm plane, but did not project as close to the lesion as in the previous specimen.

Figure 3:
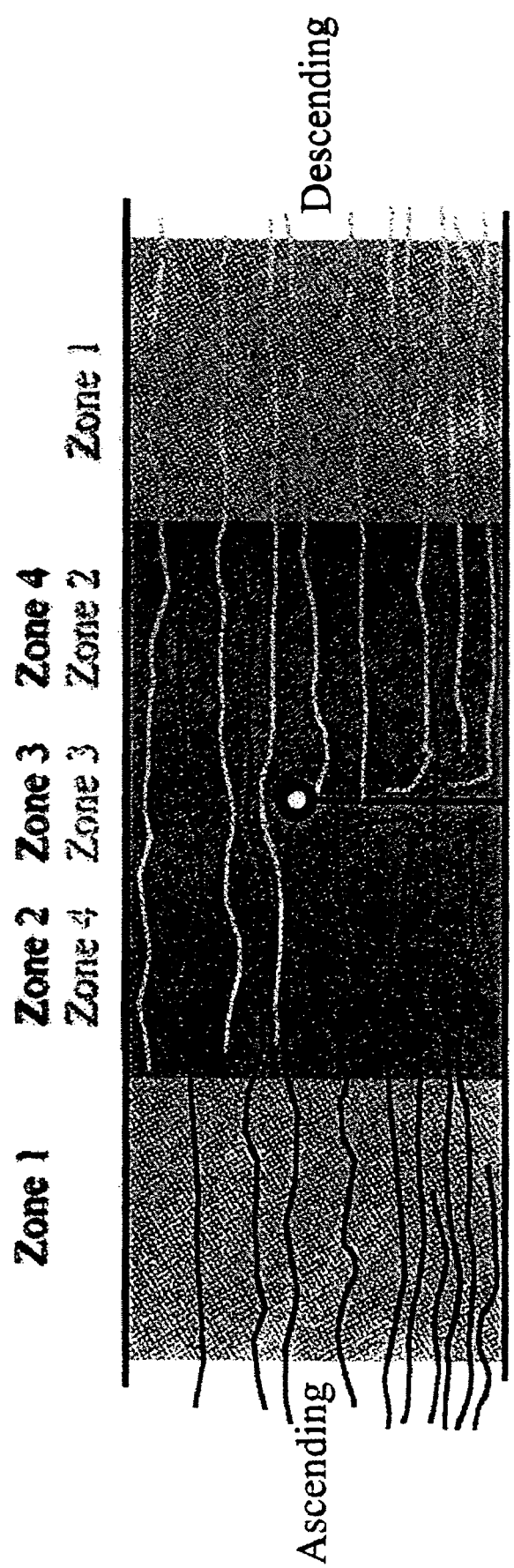
FIG. 3 represents ascending (Zones 1 to 4, moving left to right) and descending (Zones 1 to 4, moving right to left) axonal projections after experimental applications. The drawing diagrams the spinal cord with the head (rostral) end to the right and the tail (caudal) end to the left. The position of the right lateral hemisection (severing only the right side of the spinal cord) is shown as a heavy black line from the midline to the right margin of the drawing approximately in the middle of the drawing. Fibers diagrammed in light grey and black (filled from the caudal side and rostral side respectively) project well past this plane of transection (set by the position of the marker hole). On the right side of the cord, diagrammed fibers can terminate far short of the plane of transection (less than 250 µm; Zone 1) or project to within 250 µm or less (Zone 2) of the transection. Fibers were also observed terminating at the plane of transection, sometimes coursing along at its margin for short distances (Zone 3), or they were observed to project into the adjacent segment of cord by usually passing around or through the transection plane (Zone 4).

To simplify the discussion of the anatomical data, the discussion of labeled ascending and descending tracts are presented separately. Table 1 provides the comparative details of proportions of animals and the statistical comparisons between them. Though the number of spinal cords available for study was more reduced for comparisons of ascending tracts, the differences between the control group and both treatment groups was most striking. In particular, the inosine/OFS combination treatment revealed a significantly enhanced number of cords where ascending fibers were found to terminate within 250 μm ms of the lesion, and additionally at the plane of the lesion. Only two of nine control spinal cords showed fibers within 250 μms of the lesion and in only one of these could they be traced to the plane of the hemisection. Approximately 90% of the inosine/OFS-treated cords contained fibers at these locals, while in 45% of these cords axons could be traced into the rostral segment. In all three comparisons (i.e. near to, at the, or past, the plane of transection) statistical significance was reached in comparisons between the control group and the combination therapy. Statistically significantly more spinal cords treated with infusions of inosine also contained axons within 250 μm ms of the transection plane. However significance was not reached when comparing those in which axons could be traced to the plane of the cut or around and/or through it (FIG. 3).

The anterograde applications of FITC-labeled dextran to label axons within descending tracts was characterized by significantly better uptake, and better integrity, than the rhodamine-labeled dextran, although the differences in the number lost to histology between the control, inosine alone, and combined inosine plus OFS therapy was not statistically significant. The spinal cords where fibers could be traced into the caudal segment (around or through the lesion) were significant only when controls were compared to the combination therapy. When the spinal cords with fibers at the plane of transection or within 250 μm ms were compared, only the inosine-treated group was significantly different from the control preparations.

In summary, even with reduced numbers of spinal cords for evaluation, ascending tracts showed the greatest evidence of a reduction of retrograde degeneration (or dieback) of axons after transaction, and axonal regeneration in response to the experimental treatments than descending fiber tracts. Furthermore, the combination therapy was more effective in producing this result relative to controls than the inosine treatment alone.

Example 2

Effect of Combined OFS and Inosine Treatment in Clinical Cases of Paraplegia in Dogs A clinical trial of OFS in combination with inosine will be performed in dogs with naturally occurring spinal cord injuries due to intervetebral disc herniation. Criteria for admission will be as previously presented in Borgens et al. (1993) *Restor Neurol Neurosci* 5, 305–322. Briefly, criteria for selection may include one or more of the following: complete paraplegia, defined by neurological examination and electrophysiological testing; intact segmental reflexes; radiologic and myelographic evidence of spinal cord compression due to disc herniation and a focal lesion, without appreciable rostocaudal spread of necrosis; weight less than 16 kilograms. Both acute and chronic injuries may be studied. An acute injury is characterized by the onset of paralysis less than one month before treatment. A chronic injury is characterized by the onset of paralysis more than one month before treatment. Surgical implantation of the OFS device will be as previously described in Borgens et al. (1993) *Restor Neurol Neurosci* 5, 305–322. Treatment with inosine will follow the general procedures presented in Example 1. Study groups will include animals treated with OFS plus inosine and animals treated with inosine alone. Further, control groups included in the study may include any of the following, animals treated with sham OFS and sham inosine treatment, animals treated with sham OFS treatment, animals treated with sham inosine, and animals receiving no treatment. Animals will undergo neurological and electrophysiological examinations, as previously described in Borgens et al. (1993) *Restor Neurol Neurosci* 5, 305–322.

Example 3

Human Clinical Trial of OFS and Inosine Treatment

Patients with spinal cord injuries will be recruited to participate in Phase I, Phase II and Phase III clinical trials of the combined treatment with OFS and inosine, as described herein. Approval will be obtained from the appropriate Institutional Review Board. Inosine will be obtained from a supplier that follows FDA's Good Manufacturing Practices (GMP). Patients will be observed for a period of one year following treatment.

The complete disclosure of all patents, patent applications, publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method for treating a patient having a spinal cord injury, this method comprising:
   electrically stimulating the site of the spinal cord injury through the use of oscillating field stimulation; and
   administering a purine nucleoside to the patient;
   wherein nerve function through said injured spinal cord is at least partially restored;
   wherein the spinal cord injury occurred at least 100 hours prior to the combination treatment.

2. The method of claim 1 further comprising implanting a device into the patient, which device electrically stimulates the site of the spinal cord injury with oscillating field stimulation.

3. The method of claim 1 wherein the purine nucleoside comprises inosine.

4. The method of claim 1 wherein the purine nucleoside is administered to the patient systemically or locally.

5. The method of claim 1 wherein the purine nucleoside is administered orally, transdermally, interperitoneally, intravenously, or subcutaneously.

6. The method of claim 1 further comprising implanting a device into the patient, which device locally administers the purine nucleoside.

7. The method of claim 1 wherein the patient is human.

8. The method of claim 1 wherein the patient is a domestic pet.

9. The method of claim 1 wherein said restoration of nerve function is evidenced by restoration of nerve impulse conduction, a detectable increase in conduction action potentials, observation of anatomical continuity, restoration of more than one spinal root level, an increase in reflex behavior, or combinations thereof.

10. A method for treating a patient having a spinal cord injury, this method comprising:
   electrically stimulating the site of a chronic spinal cord injury through the use of oscillating field stimulation; and
   administering a purine nucleoside to the patient;
   wherein nerve regeneration at the site of the chronic spinal cord injury is stimulated;
   wherein the spinal cord injury occurred at least 100 hours prior to the combination treatment.

11. The method of claim 1, wherein the spinal cord injury occurred more than three months prior to the treatment prior to the treatment.

12. The method of claim 10, wherein the purine nucleoside is inosine, guanine, adenine, or 6-thioguanine.

13. The method of claim 10, wherein the step of electrically stimulating the site of a chronic injury occurs more than three weeks after the spinal cord injury occurs.

14. The method of claim 10, wherein the step of administering oscillating field stimulation to the patient coincides with a time when the administered purine nucleoside is present in the patient.

15. A method for treating a spinal cord injury, the method comprising the steps of:

administering inosine to a patient wherein the administering first occurs more than 100 hours after occurrence of the spinal cord injury and does not comprise intrathecal administration; and administering oscillating field stimulation to the patient more than three weeks after occurrence of the spinal cord injury, wherein nerve growth is initiated.

16. The method of claim 15, wherein the spinal cord injury is a chronic injury.

17. The method of claim 15, wherein the step of administering inosine further involves the use of a pharmaceutical carrier selected from the group consisting of water, lactated ringers solution, polyethylene glycol, or slow release capsules as a carrier for the inosine.

18. The method of claim 15, wherein the step of administering oscillating field stimulation to the patient occurs during a time when the administered purine nucleoside is present in the patient.

19. The method of claim 18, wherein the step of administering oscillating field stimulation to the patient approximately coincides with the step of administering inosine to the patient.

* * * * *